US010849566B2

(12) United States Patent
Nijsen et al.

(10) Patent No.: US 10,849,566 B2
(45) Date of Patent: Dec. 1, 2020

(54) APPARATUS, SYSTEM, METHOD AND COMPUTER PROGRAM FOR ASSESSING THE RISK OF AN EXACERBATION AND/OR HOSPITALIZATION

(71) Applicant: KONINKLIJKE PHILIPS N.V., Eindhoven (NL)

(72) Inventors: Tamara Mathea Elisabeth Nijsen, Weert (NL); Chevone Marie Barretto, London (GB); Choo Chiap Chiau, Shanghai (CN); Mareike Klee, Straelen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/321,393

(22) PCT Filed: Jun. 26, 2015

(86) PCT No.: PCT/EP2015/064487
§ 371 (c)(1),
(2) Date: Dec. 22, 2016

(87) PCT Pub. No.: WO2015/197808
PCT Pub. Date: Dec. 30, 2015

(65) Prior Publication Data
US 2017/0156681 A1  Jun. 8, 2017

(30) Foreign Application Priority Data

Jun. 27, 2014 (WO) ................ PCT/CN2014/080981
Aug. 8, 2014 (EP) ..................................... 14180307

(51) Int. Cl.
*A61B 5/11* (2006.01)
*G16H 50/30* (2018.01)
(Continued)

(52) U.S. Cl.
CPC .............. *A61B 5/7275* (2013.01); *A61B 5/08* (2013.01); *A61B 5/1118* (2013.01);
(Continued)

(58) Field of Classification Search
CPC . G16H 50/00–80; A61B 5/1114; A61B 5/112; A61B 5/1118; A61B 5/1116;
(Continued)

(56) References Cited

U.S. PATENT DOCUMENTS 7,840,346 B2 * 11/2010 Huhtala ............. A63B 24/0062
701/439
7,946,955 B2  5/2011 Koh
(Continued)

FOREIGN PATENT DOCUMENTS

RU    2449723 C1    5/2012
WO    WO9712546 A1  4/1997
(Continued)

OTHER PUBLICATIONS

Lent, "Simple Steps to Selecting the Right Accelerometer". Fierce Electronics. Mar. 1, 2009. Retrieved from <https://www.fierceelectronics.com/components/simple-steps-to-selecting-right-accelerometer> (Year: 2009).*

(Continued)

*Primary Examiner* — David J. McCrosky

(57) ABSTRACT

The present invention relates to an apparatus, a system (100), a method (200), and a computer program for assessing the risk of an exacerbation and/or hospitalization. A patient's physical activity is measured (e.g., by an accelerometer (110)) during an active period of time (e.g., during awake hours) and during a rest period of time (e.g., during sleep hours) to gather first and second activity data. A risk of exacerbation and/or hospitalization is assessed (e.g., by a risk assessment unit (120)) based on an expression involving (Continued)

the respective activity data during active and rest periods fulfilling a predetermined relationship with respect to a predetermined activity level. For instance, low activity data during active periods and high activity data during rest periods indicates an increased risk of exacerbation and/or hospital readmission for the patient.

10 Claims, 4 Drawing Sheets

(51) Int. Cl.
A61B 5/00 (2006.01)
G16H 40/63 (2018.01)
A61B 5/08 (2006.01)

(52) U.S. Cl.
CPC .......... *A61B 5/4815* (2013.01); *G16H 40/63* (2018.01); *G16H 50/30* (2018.01)

(58) Field of Classification Search
CPC ....... A61B 5/1115; A61B 5/1113; A61B 5/11; A61B 5/1101; A61B 5/1123; A61B 5/1121; A61B 5/1124; A61B 5/1126; A61B 2034/2048; A61B 2220/40; A61B 2220/44

See application file for complete search history.

(56) References Cited

U.S. PATENT DOCUMENTS

| | | |
|---|---|---|
| 2008/0275349 A1 | 11/2008 | Halperin |
| 2009/0098582 A1* | 4/2009 | Oyama .................. G16H 50/20 702/19 |
| 2010/0010552 A1 | 1/2010 | Wilson |
| 2010/0204615 A1* | 8/2010 | Kyle .................. A63B 24/0006 600/595 |
| 2013/0030258 A1 | 1/2013 | Cheung |
| 2013/0053817 A1* | 2/2013 | Yun .......................... A61M 5/00 604/500 |
| 2017/0032099 A1* | 2/2017 | Cales ..................... G16H 50/30 |

FOREIGN PATENT DOCUMENTS

| | | |
|---|---|---|
| WO | WO2005056107 A1 | 6/2005 |
| WO | WO2011073815 A2 | 6/2011 |
| WO | WO2012020433 A1 | 2/2012 |
| WO | WO2013080109 A2 | 6/2013 |

OTHER PUBLICATIONS

Kurcalte I. et al., "Circadian Heart Rate Variability in Permanent Atrial Fibrillation Patients", Electrocardiology 2014—Proceedings of the 41st International Congress on Electrocardiology, Jun. 7, 2014 (Jun. 7, 2014), XP055147062, URL: http://www.measurement.sk/1CE2014/proceedings/161.pdf [retrieved on Oct. 16, 2014].

Tukek, Tufan et al., "Effect of Diurnal Variablity of heart Rate on Developemnt of Arrhythmia in Patients with Chronic Obstructive Pulmonary Disease", International Journal of Cardiology, 88 (2003) 199-206.

* cited by examiner

APPARATUS, SYSTEM, METHOD AND COMPUTER PROGRAM FOR ASSESSING THE RISK OF AN EXACERBATION AND/OR HOSPITALIZATION

CROSS-REFERENCE TO RELATED APPLICATIONS

This patent application claims the priority benefit under 35 U.S.C. § 371 of international patent application no. PCT/EP2015/064487, filed Jun. 26, 2015, which claims the benefit of international patent application no. PCT/CN2014/080981, filed Jun. 27, 2014, which claims the benefit of European Application No. EP14180307.2 filed Aug. 8, 2014. These applications are hereby incorporated by reference herein.

FIELD OF THE INVENTION

The invention relates to an apparatus for assessing the risk of an exacerbation and/or hospitalization of a subject, a system for assessing the risk of an exacerbation and/or hospitalization of a subject, to a method for assessing the risk of an exacerbation and/or hospitalization of a subject, and to a computer program for assessing the risk of an exacerbation and/or hospitalization of a subject.

BACKGROUND OF THE INVENTION

Chronic Obstructive Pulmonary Disease (COPD) is a respiratory disease that is characterized by inflammation of the airways. COPD is characterized by an airflow limitation that is not fully reversible. The airflow limitation is both progressive and associated with an abnormal inflammatory response of the lungs to noxious particles or gases. Symptoms of COPD may include coughing, wheezing and the production of mucus, and the degree of severity may, in part, be viewed in terms of the volume and color of secretions.

Exacerbations are the worsening of COPD symptoms. The exacerbations may be associated with a variable degree of physiological deterioration. The exacerbations may be measured as a decrease in Forced Expiratory Volume measured over one second ($FEV_1$). The exacerbations may be characterized by increased coughing, dyspnea (i.e., shortness of breath) and production of sputum. The major symptom of an exacerbation is the worsening of dyspnea (i.e., shortness of breath) while the main reaction is a lack of energy, which in turn may translate to a reduction in physical activity levels.

The exacerbations are normally caused by viral or bacterial infections and often may lead to hospitalization of the COPD patients. The frequency of exacerbations increases during the winter months due to cold stresses on the patient's body as disclosed in the article "Seasonal distribution of COPD exacerbations in the Prevention of Exacerbations with Tiotropium in COPD trial" by Rabe et al., 2013 March; 143(3):711-9. This may be due to a combination of a) the cooling of facial skin and airways, resulting in bronchoconstriction, and b) the thermoregulatory system becoming less effective with age, thus making COPD patients more susceptible for respiratory infections. The exacerbations not only limit the performance of daily activities, but also significantly decrease the health related quality of life of COPD patients. A high frequency of exacerbations is linked to a poor prognosis for survival. Also, the exacerbations often may result in hospitalization, which is the main determinant of the overall healthcare expenditure for COPD patients.

Because of the damage done when an exacerbation takes place it is desirable to predict the likely onset of an exacerbation and initiate treatments which either prevent the occurring exacerbation and/or treat the symptoms at an early stage thereby reducing the severity and damage caused by the exacerbation. Moreover, reducing and most importantly preventing exacerbations may help COPD patients lead an improved quality of life and may lower the healthcare costs for COPD patients.

Change of activity, in particular, a change in the intensity of a physical activity, is often mentioned as a good measure to detect exacerbations in COPD. So far, numerous approaches have been considered when studying the physical activities of COPD patients, see the article "Physical activity and hospitalization for exacerbation of COPD" by Pitta et al., Chest. 2006 March; 129(3):536-44, the article "Characteristics of physical activities in daily life in chronic obstructive pulmonary disease" by Pitta et al., Am J Respir Crit Care Med. 2005 May 1; 171(9):972-7. Epub 2005 Jan. 21, and the article "Physical activity and clinical and functional status in COPD" by Garcia-Aymerich et al., Chest. 2009 July; 136(1):62-70. doi: 10.1378/chest.08-2532. Epub 2009 Mar. 2. For example, different types of activity (such as, e.g., walking, standing, sitting, running) performed by patients have been actively studied by many researchers. Further, counting the number of steps experienced by the patient has also been looked into. All these approaches however only examine the activity of patients during their active period, such as, e.g., during day time. The symptoms of COPD do not stop when patients go to bed, of course. In many occasions, COPD patients cannot enjoy a good night sleep because of their symptoms (such as, e.g., coughing). Nonetheless, the existing studies mentioned above do not continuously study patients' activity during sleep in the home environment, i.e., during bed time in relation with hospital readmissions. The article "Actigraphic assessment of sleep in chronic obstructive pulmonary disease" by Nunes et al., Sleep Breath. 2013 March; 17(1):125-32, studies twenty-six moderate to very severe COPD patients and fifteen controls by actigraphy for at least five days. COPD patients showed increased sleep latency, mean activity, and reduced total sleep time as compared to the controls.

Embodiments of the disclosure of WO 2013/080109 A2 provide for a health monitoring system comprising an activity monitor. The health monitoring system further comprises a processor and a memory for storing machine readable instructions. The instructions cause the processor to derive activity counts from the activity data acquired by the activity monitor. The instructions further cause the processor to store the activity counts in the memory, and are associated with a time. The instructions further cause the processor to calculate at least two statistical parameters from the activity counts, wherein the at least two statistical parameters are descriptive of the activity counts as a function of time. The instructions further causes the processor to calculate a risk score for each of the at least two statistical parameters. The instructions further cause the processor to calculate a total risk score using the risk score for each of the at least two statistical parameters.

A computer-implemented method for predicting an onset of an exacerbation in a COPD patient is provided by US 2013/0030258 A1. The method includes measuring physical activity of the patient over a period of time to gather physical activity data; measuring a respiration characteristic of the patient over the period of time to gather respiration data; and executing, on one or more computer processors, one or more computer program modules to detect the onset of the exacerbation based on predetermined criteria, wherein the predetermined criteria comprises a comparison of a change in the respiration data with a change in the physical activity data.

SUMMARY OF THE INVENTION

It is an object of the present invention to provide an improved apparatus, system, method, and computer program for predicting and assessing the risk of an exacerbation and/or hospitalization, specifically for the case of a COPD patient. In particular, it is desired to improve the existing approaches by considering a patient's physical activity during night as well.

In a first aspect of the invention, there is provided an apparatus for assessing the risk of an exacerbation and/or hospitalization of a subject, said apparatus comprising: an input unit for receiving first and second activity data for said subject; wherein said first activity data is indicative of said subject's physical activity during at least part of an active period of time; wherein said second activity data is indicative of said subject's physical activity during at least part of a rest period of time; and a risk assessment unit configured to detect an onset of the exacerbation based on predetermined criteria, wherein the predetermined criteria comprises the condition that an expression involving the first activity data and/or the second activity data fulfills a predetermined relationship with respect to a predetermined activity level, wherein a) the apparatus is configured to compare the first activity data to a first activity level; and to compare the second activity data to a second activity level, wherein the first activity level is higher than the second activity level, wherein the predetermined criteria comprise the conditions that (1) the first activity data is lower than the first activity level, and (2) the second activity data is higher than the second activity level, b) the apparatus is configured to determine a ratio between first activity data and second activity data, wherein the apparatus is configured to compare the ratio to a ratio activity level, wherein the predetermined criteria comprise the condition that the ratio is lower than the ratio activity level, and/or c) the apparatus is configured to determine a difference between first activity data and second activity data, wherein the apparatus is configured to compare the difference to a difference activity level, and wherein the predetermined criteria comprise the condition that the difference is lower than the difference activity level.

In a second aspect of the invention, there is provided a system for assessing the risk of an exacerbation and/or hospitalization of a subject. The system comprises: a physical activity measurement unit; wherein the physical activity measurement unit is configured to measure the subject's physical activity during at least part of an active period of time to gather first activity data (active period activity data); wherein the physical activity measurement unit is further configured to measure the subject's physical activity during at least part of a rest period of time to gather second activity data (rest period activity data); and an apparatus as defined in the first aspect; wherein said input unit of said apparatus is configured to receive said first and second activity data from said physical activity measurement unit.

As noted above, change of activity, in particular, a change in the intensity of a physical activity is often mentioned as a good measure to detect the deterioration of the subject (such as, e.g., a patient) and/or the onset of an exacerbation in COPD. The existing approaches however only examine the activity of subjects (such as, e.g., patients) during their active period, such as, e.g., during day time. The symptoms of COPD do not stop when patients go to bed, of course. In many occasions, COPD patients cannot enjoy a good night sleep because of their symptoms (such as, e.g., coughing). According to the first and second aspects of the present invention, it is proposed to use a patients' physical activity during both active (such as, e.g., day time) as well as rest (such as, e.g., sleep) time periods. The proposed system may comprise a device, which is worn or carried by the patient so as to continuously measure physical activity data. Alternatively, the system may comprise a physical activity measurement unit, such as, e.g., an accelerometer, which is worn, e.g. on the patient's wrist, and which is in communication with a risk assessment unit, which may be comprised in a personal computer or the like. The risk assessment unit may be embodied by a computer program product causing a processor to analyze the physical activity data gathered from the patient during active and rest periods. It is observed that unstable COPD patients (i.e., patients with an increased risk of readmission within the monitoring period, e.g., one month post discharge) exhibit increased activity during sleep (e.g., because they are kept awake by symptoms such as, e.g., their cough) and a decreased activity during awake hours (e.g., because they are tired and exhausted from not having had a good night of sleep). A combination of physical activity data gathered during active time periods with physical activity data gathered during rest time periods may thus be used beneficially to provide an improved risk stratification for hospitalization based, e.g., on a change in daily activity and sleep of COPD patients.

The term "risk", as used herein, corresponds to the likelihood of a (potentially unpleasant) event (namely, an exacerbation and/or hospitalization) to occur and thus ranges between 0% (exacerbation and/or hospitalization can be excluded) and 100% (exacerbation and/or hospitalization is certain to occur). On the other hand, the term "onset" as used herein corresponds to the beginning of something, especially something unpleasant (such as an exacerbation, which may lead to hospitalization of the subject). "Exacerbation risk" and "exacerbation onset" are related in that detecting an onset of an exacerbation usually corresponds to a higher risk of an actual exacerbation occurring. It is noted however that the "onset", as used herein, does not refer to a likelihood, but rather to a trigger or a flag, which signals that a given criteria indicative of an increased exacerbation or hospitalization is fulfilled.

According to option a), the apparatus is configured to compare the first activity data to a first activity level; and/or the apparatus is configured to compare the second activity data to a second activity level. Comparing activity data to activity levels (such as, e.g., thresholds, upper limits, and/or lower limits) advantageously addresses the fact that a typical patient exhibits different average activity levels during active and rest periods. Namely, even for a healthy person, activity data during a rest period will be low. Differentiating between active and rest periods thus involves the advantage that low activity during rest periods is not misinterpreted as an overall low activity (which would potentially be interpreted as an increased readmission risk).

Here, the first activity level is higher than the second activity level. This option thus takes into account that an average activity level during an active period is usually higher than an average activity level during rest period.

Further, the predetermined criteria comprises the conditions that (1) the first activity data is smaller than the first activity level, and (2) the second activity data is higher than the second activity level. Typically, as explained in more detail herein below, an unstable COPD patient is more restless at night (i.e., exhibiting higher activity data during the rest period), but tired during the day (i.e., exhibiting less activity data during the active period). In contrast, a stable COPD patient with a lower risk of readmission within the monitoring period, e.g., one month post discharge, typically exhibits less movement during sleep (i.e., less activity during rest period), and is more active during the day (i.e., increased activity during active period).

According to option b), the apparatus is configured to determine a ratio between first activity data and second activity data. By considering ratios, the preferred embodiment achieves a reduced dependency on the physical activity measurement unit (e.g., accelerometer) used. This is because the absolute values of physical activities are ignored in favor of a ratio of first and second activity data. Put differently, a first accelerometer may yield very high absolute values of activity data (e.g., because the first accelerometer is very sensitive), whereas a second accelerometer may yield very low absolute values of activity data (e.g., because the second accelerometer is less sensitive). In this case, comparing the absolute values to predetermined thresholds will lead to a different result, depending on the accelerometer used. Considering ratios of activity data however is less prone to specific details of the accelerometer, as long as the accelerometer output is approximately proportional to the patient's physical activity. Preferably, the total daily awake activity counts and the total daily sleep activity counts are acquired, and their ratio is computed. This way, the duration of active and rest periods is taken into account. Alternatively and/or additionally, the daily mean awake activity counts and the daily mean sleep activity counts are determined, and their ratio is computed.

Here, the apparatus is configured to compare the ratio to a ratio activity level. Preferably, the ratio activity level may correspond to an average activity level of a patient group. For instance, if the ratio is equal to or larger than the average activity level of a group of stable COPD patients who have a lower risk of having an exacerbation or readmission during the monitoring period (i.e., for instance, first activity data is high and second activity data is low), the risk of an exacerbation and/or hospitalization is low. On the other hand, if the ratio is smaller than the average activity level of a group of unstable COPD patients (i.e., for instance, first activity data is low and second activity data is high), the risk of an exacerbation and/or hospitalization may be high.

Further, the predetermined criteria comprise the condition that the ratio is smaller than the ratio activity level. This preferred embodiment makes use of the fact that if the ratio is smaller than the average activity level of a group of unstable COPD patients (i.e., for instance, first activity data is low and second activity data is high), the risk of an exacerbation and/or hospitalization may be high.

According to option c), the apparatus is configured to determine a difference between first activity data and second activity data. Here, the apparatus is configured to compare the difference to a difference activity level. The difference activity level may correspond to, e.g., a threshold. Further, the predetermined criteria comprise the condition that the difference is lower than the difference activity level.

According to a preferred embodiment, the first activity data corresponds to average activity data of said subject (e.g., a patient) during at least part of the active period; and/or the second activity data corresponds to average activity of said subject (e.g., a patient) during at least part of the rest period.

By considering average activity data, the apparatus according to the preferred embodiment is more robust with regard to fluctuations, because only average activity data is considered. It shall be understood that the preferred embodiment likewise may refer to considering a median of activity data. Further, it shall be understood that the average and/or the median may be determined after discarding the highest and lowest activity data measurements in order to be more robust against single outliers.

According to a further preferred embodiment, the first activity data corresponds to average activity data of said subject (e.g., a patient) during the entire active period; and/or the second activity data corresponds to average activity of said subject (e.g., a patient) during the entire rest period. By considering average activity over an entire active and/or rest period, the preferred embodiment is more robust with regard to fluctuations, which are limited to brief time periods.

According to a further preferred embodiment, the apparatus is configured to compare the first activity data to past first activity data, wherein the past first activity data correspond to first activity data gathered on one or more previous days; and/or the apparatus is configured to compare second activity data to past second activity data, wherein the past second activity data correspond to second activity data gathered on the one or more previous days. By comparing the patient's activity data for a given day to the patient's activity data of the previous day(s), the preferred embodiment enables the monitoring of a time evolution of the COPD patient's activity. Preferably, in order to be able to employ past first and second activity data, the system is configured to write to and read from a data storage. Said data storage may be part of said system. In another embodiment, said data storage may be accessed via networking means such as but not limited to the internet.

According to a further preferred embodiment, the predetermined criteria comprises the conditions that (1) the first activity data is lower in comparison to first activity data when not at risk and (2) the second activity is higher in comparison to first activity data when not at risk. As explained in more detail herein below, an increased activity level during rest periods and a decreased activity level during active periods may typically indicate an increased risk for an exacerbation or hospital readmission during the monitoring period.

According to a further preferred embodiment, the predetermined criteria comprises the conditions that (1) the first activity data is smaller than one or more of past first activities, and (2) the second activity is higher than one or more of past second activities. As explained in more detail herein below, an increased activity level during rest periods and a decreased activity level during active periods may typically indicate an increased risk for an exacerbation or hospital readmission during the monitoring period.

According to a further preferred embodiment, the apparatus is configured to compare the ratio to past ratios, wherein the past ratios correspond to ratios between first activity data and second activity data gathered on one or more previous days. By comparing the measured ratio for a given day to the measured ratio of the previous day(s), the preferred embodiment enables monitoring of a time evolution of the COPD patient's activity.

According to a further preferred embodiment, the predetermined criteria comprise the condition that the ratio is smaller than one or more of past ratios. Typically, an increased activity level during rest periods and a decreased activity level during active periods may indicate an increased risk for hospital readmission. Accordingly, a decreased ratio (i.e., activity data during rest period high and activity data during active periods low) may indicate an increased risk of an exacerbation or hospital readmission. Continuous low ratios can indicate an increased risk of an exacerbation or hospital readmission. Note that one day with a low ratio might not necessarily mean increased risk of an exacerbation. However, if a continuously low ratio persists over some days this would be an indication for an increased risk of an exacerbation.

According to a further preferred embodiment, the apparatus is configured to determine a difference between first activity data and second activity data. Stable COPD patients who have a lower risk of having an exacerbation or readmission during the monitoring period have a high value for the difference between the activity level during active periods minus activity level during the rest periods. With a low activity level during the rest period in these patients, this difference can be close to the activity level during active periods. Unstable COPD patients who have a higher risk of having an exacerbation or readmission during the monitoring period have a much lower value for the difference between the activity level during active periods minus activity level during the rest periods, e.g., the first activity data is low compared to stable situation and the second activity data is high compared to stable situation, resulting in a smaller difference.

According to a further preferred embodiment, the apparatus is configured to divide a difference between daily awake activity count and sleep activity count by the total daily activity count.

According to a further preferred embodiment, the apparatus is configured to determine the fraction of daily activity count occurring during sleep by dividing the sleep activity count by the total daily activity count.

According to a further preferred embodiment, the apparatus further comprises an alarm configured to generate an alarm indication to the patient and/or to the patient's physician or caretaker, when the predetermined criteria are satisfied. Preferably, the alarm may notify the patient, when an increased exacerbation and/or readmission risk occurs. Alternatively and/or additionally, the alarm may notify the physician or caretaker directly.

According to a further preferred embodiment, the physical activity measurement unit comprises an accelerometer and/or a piezoelectric sensor.

In a third aspect of the invention, there is provided a method for assessing the risk of an exacerbation and/or hospitalization. The method comprises measuring the patient's physical activity during at least part of an active period of time to gather first activity data; measuring the patient's physical activity during at least part of a rest period of time to gather second activity data; assessing the risk of an exacerbation and/or hospitalization based on predetermined criteria, wherein the predetermined criteria comprises the condition that an expression involving the first activity data and/or the second activity data fulfills a predetermined relationship with respect to a predetermined activity level. Further, the method comprises a) comparing the first activity data to a first activity level; and comparing the second activity data to a second activity level, wherein the first activity level is higher than the second activity level, wherein the predetermined criteria comprise the conditions that (1) the first activity data is lower than the first activity level, and (2) the second activity data is higher than the second activity level; b) determining a ratio between first activity data and second activity data, and comparing the ratio to a ratio activity level, wherein the predetermined criteria comprise the condition that the ratio is lower than the ratio activity level, and/or c) determining a difference between first activity data and second activity data, and comparing the difference to a difference activity level, wherein the predetermined criteria comprise the condition that the difference is lower than the difference activity level.

In a fourth aspect of the invention, there is provided a computer program for assessing the risk of an exacerbation and/or hospitalization, the computer program comprising program code means for causing a system for assessing the risk of an exacerbation and/or hospitalization as defined in the first aspect to carry out the steps of the method for assessing the risk of an exacerbation and/or hospitalization as defined in the third aspect, when the computer program is run on a computer controlling the system for assessing the risk of an exacerbation and/or hospitalization.

It shall be understood that the apparatus for assessing the risk of an exacerbation and/or hospitalization claim 1, the system for assessing the risk of an exacerbation and/or hospitalization claim 8, the method for assessing the risk of an exacerbation and/or hospitalization of claim 9 and the computer program for assessing the risk of an exacerbation and/or hospitalization of claim 10 have similar and/or identical preferred embodiments as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
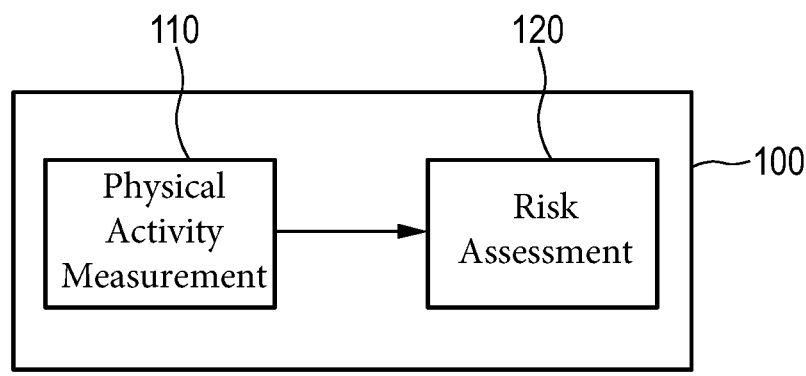
FIG. 1 shows schematically and exemplarily an embodiment of a system for assessing the risk of an exacerbation and/or hospitalization.

FIG. 1 shows schematically and exemplarily an embodiment of a system 100 for assessing the risk of an exacerbation and/or hospitalization. The system 100 comprises a physical activity measurement unit 110 and a risk assessment unit 120. The physical activity measurement unit 110 is configured to measure the patient's physical activity during at least part of an active period of time to gather first activity data. The physical activity measurement unit 110 is further configured to measure the patient's physical activity during at least part of a rest period of time to gather second activity data. The risk assessment unit 120 is configured to detect the onset of the exacerbation based on predetermined criteria. The predetermined criteria comprises the condition that an expression involving the first activity data and/or the second activity data fulfills a predetermined relationship with respect to a predetermined activity level.

Figure 2:
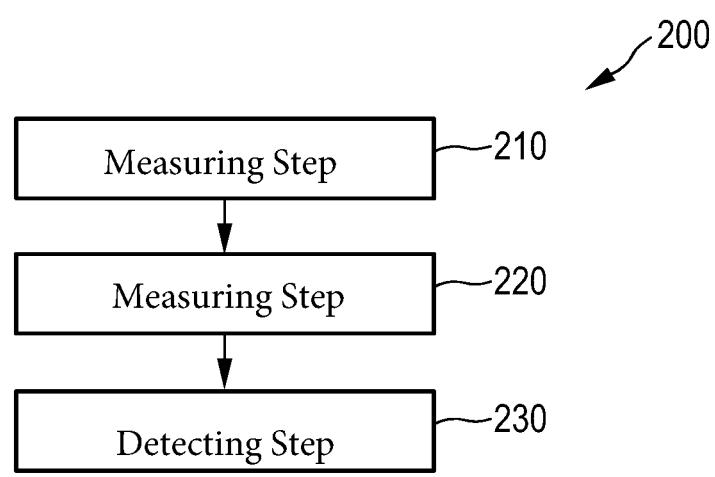
FIG. 2 shows schematically and exemplarily an embodiment of a method for assessing the risk of an exacerbation and/or hospitalization.

FIG. 2 shows schematically and exemplarily an embodiment of a method 200 for assessing the risk of an exacerbation and/or hospitalization. The method 200 comprises measuring (step 210) the patient's physical activity during at least part of an active period of time to gather first activity data; measuring (step 220) the patient's physical activity during at least part of a rest period of time to gather second activity data; and detecting (step 230) the onset of the exacerbation and/or the hospitalization risk based on predetermined criteria. The predetermined criteria comprises the condition that an expression involving the first activity data and/or the second activity data fulfills a predetermined relationship with respect to a predetermined activity level.

According to a first preferred embodiment, measurements on physical activity taken during active and rest periods of the day are used as an indication of whether a COPD patient discharged from the hospital is recovering well or whether the patient is at risk for readmission.

Figure 3:
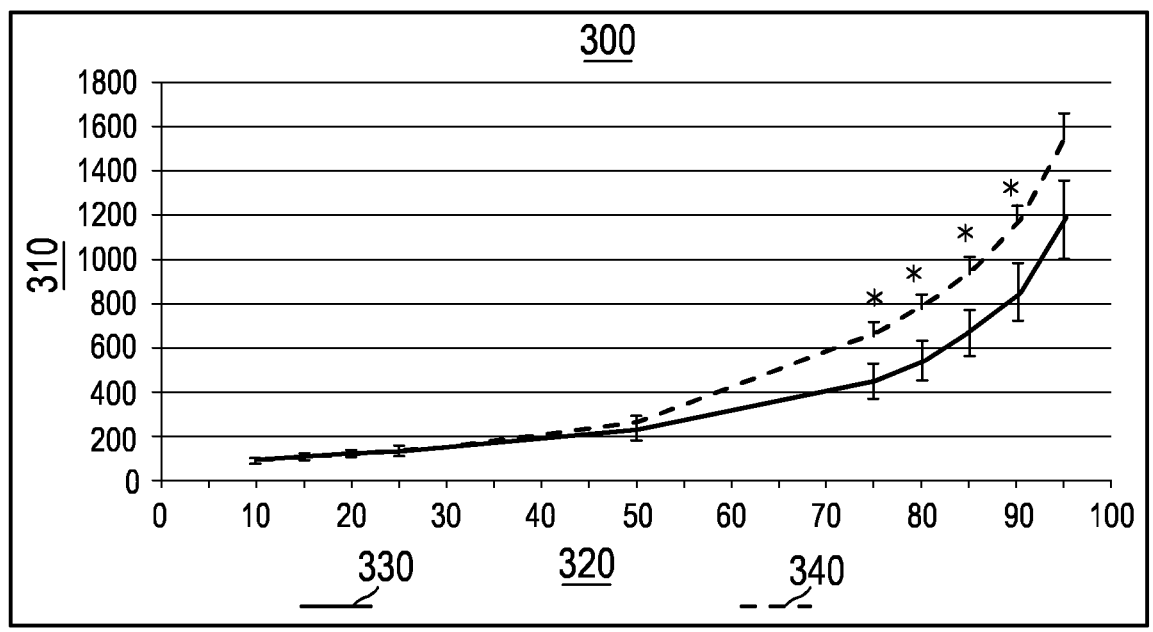
FIG. 3 shows schematically and exemplarily activities of patients from two different groups during an active period.
Figure 4:
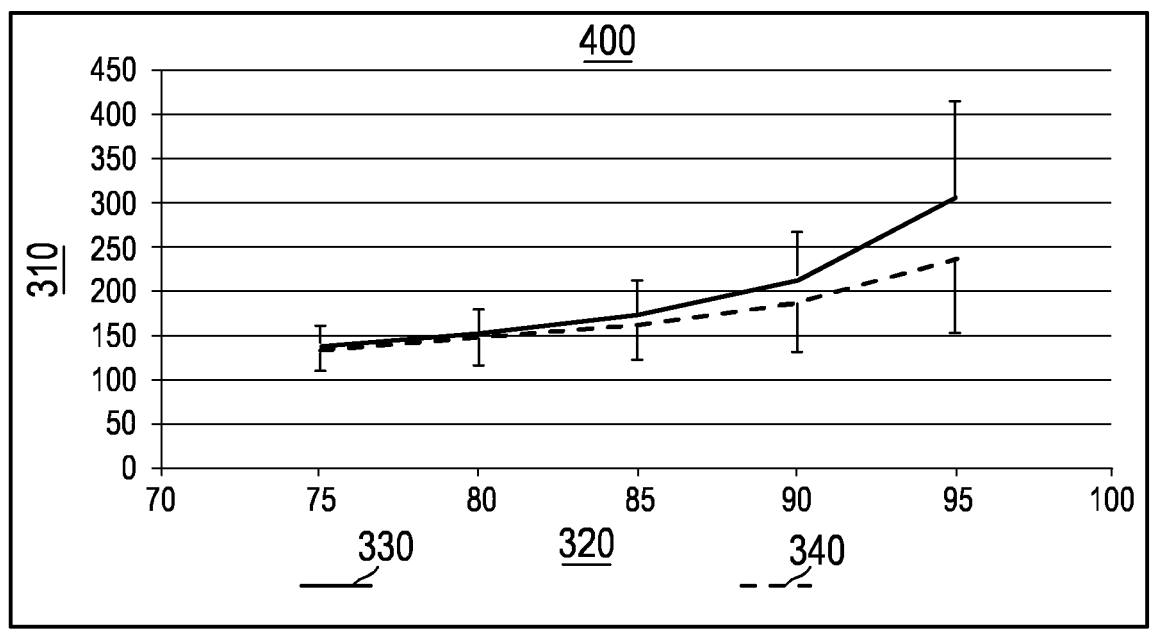
FIG. 4 shows schematically and exemplarily activities of patients from two different groups during a rest period.

Graph 300 in FIG. 3 shows schematically and exemplarily activities of patients (in counts/min on axis 310) from two different groups 330 and 340 during an active period with regard to the percentile level 320 for each patient. The absolute value of "counts/minute" is arbitrary and depends on the activity detection device. The activity count depends upon where the device is worn (which can be standardized to the wrist) and how the acceleration data (standard, $m/s^2$) is processed to calculate the activity "counts". The processing of the acceleration data varies among device manufacturers but can be standardized. For each patient, an average physical activity has been determined over a period of time and is included in the graph 300, where the errors show the respective statistical error. In other words, the plot shows mean physical activity counts belonging to the corresponding percentile together with the statistical range "mean+/− s.e. (statistical error)". The average has been taken across all days of data available for the patient. Herein, the term "active" denotes generally that the patient may be engaging or ready to engage in physically energetic pursuits, or simply that the patient is awake, i.e., not sleeping. In the example of FIG. 3, the active period corresponds to a 14-hour period. In other examples, the active period may correspond to longer or shorter time periods. Further, the active period may comprise a plurality of separate time periods, which are not necessarily continuous. For instance, a patient may take a nap in the early afternoon and resume an activity afterwards. In such a case, the time period during which the patient naps may be discarded from the active period data. Graph 400 of FIG. 4 shows schematically and exemplarily activities of patients from the same two groups 330 and 340 during a rest period. Again, physical activity 310 is shown in counts/min over the group percentile 320. Herein, the term "rest" denotes generally that the patient may not move, relax, sleep, or recover strength, or simply that the patient is sleeping, i.e., not awake. In the example of FIG. 4, the rest period corresponds to a 7-hour period. In other examples, the rest period may correspond to longer or shorter time periods. Further, the rest period may comprise a plurality of separate time periods, which are not necessarily continuous. For instance, a patient may have already gone to bed, but decides to get up again, e.g., to watch TV. In such a case, the time period during which the patient is awake (e.g., because the patient watches TV) may be discarded from the rest period data.

As noted above, in the example of FIGS. 3 and 4, the absolute value of "counts/minute" is arbitrary and may depend, e.g., on the physical activity measurement unit 110 (for instance, an accelerometer) used. For each patient, an average physical activity has been determined over a period of time (such as, e.g., several days), e.g., immediately after hospital discharge, and is included in the graph, where the error bars show the respective statistical error for a data point. The representation of, e.g., FIG. 3, yields that the 80th percentile of group 1 (i.e., the activity level below which each person of group 1 spent 80% of his/her awake time), denoted by reference numeral 330, corresponds to ca. 650 counts/min, whereas the 80th percentile of group 2 (i.e., the activity level below which each person of group 2 spent 80% of his/her awake time), denoted by reference numeral 340, corresponds to ca. 950 counts/min. In other words, Group-1-patients 330 on average exhibit an activity of no more than 650 counts/min during 80% of their awake time, whereas Group -2-patients 340 on average exhibit an activity of no more than 950 counts/min during 80% of their awake time.

In particular, physical activity data from two groups of COPD patients are compared. Group-1-patients are COPD patients with hospital readmission experience due to an exacerbation. Group-2-patients are COPD patients without any further hospital readmission experience since their physical activity data is collected. In this regard, Group-2-patients may be considered more stable than Group-1-patients, because Group-2-patients have no further hospital readmission experience.

FIG. 3 shows that patients from Group 1 are less active than patients from Group 2 during an active period (such as, e.g., during the day). FIG. 4 shows that patients from Group 1 are more active than patients from Group 2 during a rest period (such as, e.g., during patients' bed time). One possible reason for this observation is that patients in Group 1 experience more disturbances from their symptoms (such as, e.g., coughing during the night) when compared to stable patients (i.e., patients in Group 2).

The results of FIGS. 3 and 4 may be used as follows to predict readmission risk for COPD patients. According to one example, a risk assessment unit 120 compares patient's activity during active hours to a first activity level, and a patient's activity during REST hours to a second activity level. The first activity level is preferably higher than the second activity level. If the patient's activity during active hours is less than the first activity level and if the patient's activity during rest hours is more than the second activity level, there is an increased risk for readmission. First and second activity levels may be determined, e.g., from previous patients falling into one of Group 1 or Group 2. Note that, as noted above, the absolute value of activity counts is arbitrary or, to be precise, may depend on the actual activity measurement device used. Thus, determining first and second activity levels may be tied to the specific type of physical activity measurement unit 110 (such as, e.g., an accelerometer) used. In other words, first and second activity levels (or cut-off values) are not arbitrary, but they are a function of the specific accelerometer used. The activity count depends upon where the device is worn (which can be standardized to the wrist) and how the acceleration data (standard, m/s$^2$) is processed to calculate the activity "counts". Processing of the acceleration data varies among device manufacturers but can be standardized. Another possibility to use the results of FIGS. 3 and 4 to predict readmission risk for COPD patients is to use day night values and day night ratios as features and use other classification schemes besides single thresholds (such as, e.g., linear regression, logistic regression, support vector machines, etc.).

According to further preferred embodiments, ratio measurements (and/or difference measurements) on physical activity taken during active and rest periods of the day are used as an indication whether a COPD patient discharged from the hospital is recovering well or whether the patient is at risk of an exacerbation and/or hospital readmission.

Figure 5:
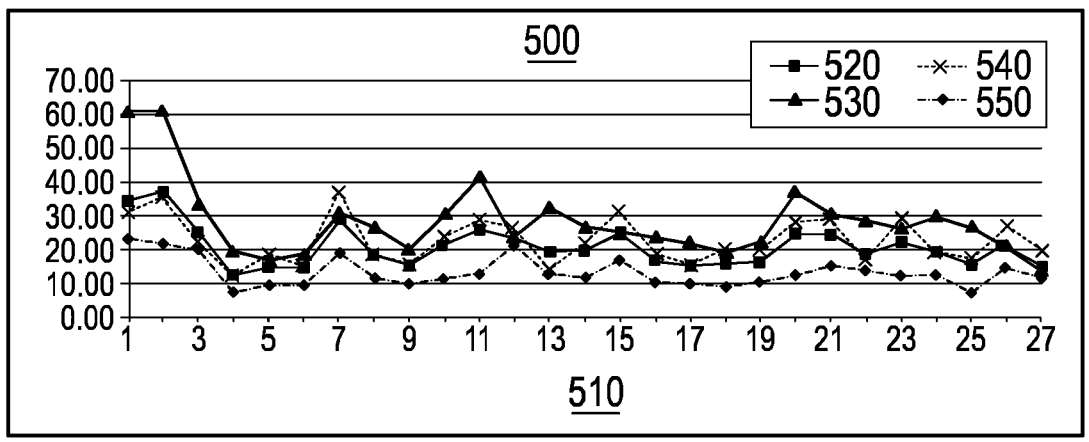
FIG. 5 shows schematically and exemplarily the ratio of mean awake activity count and mean sleep activity count for a stable patient.
Figure 6:
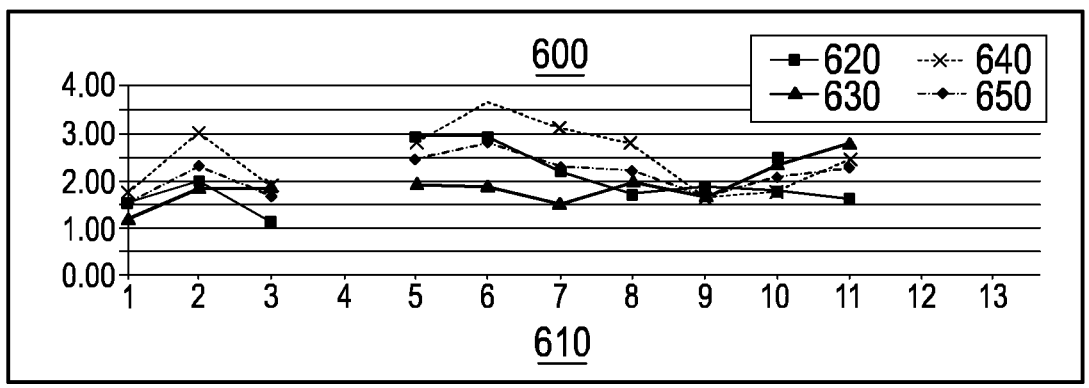
FIG. 6 shows schematically and exemplarily the ratio of mean awake activity count and mean sleep activity count for a patient who is readmitted to hospital on day 11.

Graph 500 of FIG. 5 shows schematically and exemplarily the ratio of mean active (e.g., awake) activity count and mean rest (e.g., sleep) activity count for a COPD patient who did not have an exacerbation or a readmission within the monitoring period (such as, e.g., a patient from Group 2 mentioned herein above) with respect to the number of days after discharge from the hospital (axis 510). Reference numerals 520, 530, 540, and 550 denote the ratios between total awake activity count and sleep activity count, morning awake activity count and sleep activity count, afternoon awake activity count and sleep activity count, and evening awake activity count and sleep activity count, respectively. Graph 600 of FIG. 6 shows schematically and exemplarily the ratio of mean active (e.g., awake) activity count and mean rest (e.g., sleep) activity count for a COPD patient who is readmitted to hospital on day 11 (i.e., a patient who may belong to Group 1 mentioned herein above) with respect to the number of days after discharge from the hospital (axis 610). Reference numerals 620, 630, 640, and 650 denote the ratios between total afternoon activity count and sleep activity count, morning awake activity count and sleep activity count, evening awake activity count and sleep activity count, and total awake activity count and sleep activity count, respectively. The suggested method is reliable in detecting hospital admissions and simpler than previous approaches, because only need a physical activity measurement unit 110 (such as, e.g., an accelerometer) is needed to for determining exacerbation risk.

In a preferred embodiment, absolute ratio values may be used alternatively or in addition to a ratio tendency (i.e., to a time evolution of ratios). As noted above, ratio measurements are independent (or at least only weakly dependent) of the actual activity measurement device used (since the absolute number of counts/min is irrelevant for the determined ratio). Another preferred embodiment (described below) relates to using a scaled difference, where the difference between first activity data (active period activity data) and second activity data (rest period activity data) is divided by the sum of first activity data and second activity data. With such an embodiment, first, a constant offset in activity counts for a given accelerometer will be cancelled from the measurement result. Second, the approach is less prone to an accelerometer's sensitivity, because the difference in activity counts is divided by the sum of activity counts so that the same threshold can be used regardless of the accelerometer used. The respective ratio levels (or thresholds) may thus be determined regardless of the details of the activity measurement device used to measure physical activity. Thus, the ratio levels from FIGS. 5 and 6 may be used to determine an average ratio for Group-1-patients and Group-2-patients. From this, a ratio activity level may be determined to correspond to, e.g., a ratio halfway between the average ratios for Group-1- and Group-2-patients. Accordingly, a risk of an exacerbation and/or readmission may be predicted for a patient based on evaluating a single day's activity for that patient (and comparing it to Groups 1 and 2) rather than comparing it to the patient's data for previous days.

In other words, Graph 500 of FIG. 5 shows the data of a patient that recovers well. As can be seen from FIG. 5, in general the ratio between day and night is high. This means that the patient is more active during the day than during the night.

Graph 600 of FIG. 6 shows the data of a patient who is readmitted to the hospital on day 11. As can be seen when comparing FIG. 6 to FIG. 5, the ratio between activity counts during active and rest periods is much lower for the readmitted patient compared to patients that are stable. Data for day 4 are missing in FIG. 6 because the patient did not wear the sensor on this particular day (this leads to missing data points).

Preferably, a system 100 according to a preferred embodiment comprises a physical activity measurement unit 110 configured for measuring a patient's physical activity during at least a part of an active period and at least a part of a rest period. More preferably, the physical activity measurement unit 100 is configured for measuring a patient's physical activity during the entire active period and during the entire rest period. According to an even further preferred embodiment, the physical activity measurement unit 110 is configured for measuring a patient's physical activity for 24 hours per day. Preferably, the physical activity measurement unit 110 may comprise an accelerometer that will collect the physical movement of patients in three dimensions (such as, e.g., x, y, and z direction). However, any physical activity measurement unit capable of detecting physical motion is suitable. In fact, any other method that can continuously monitor physical activity could be used.

In order to separate the active and rest periods, the system 100 preferably comprises an algorithm configured for detecting the moment when a patient goes to bed. Preferably, the algorithm is configured for detecting when a patient wakes up from sleep. Different options are available to differentiate active and rest periods. For instance, one may define time periods with a high likelihood of falling into one category (e.g. the time period between midnight and 4 am would correspond to a rest period, whereas the time period between 10 am and 5 pm would correspond to an active period. Alternatively and/or additionally, rest and active periods may be determined on a patient-by-patient basis. Preferably, the time of the day, and/or activity levels, and/or a light intensity (which may, e.g., be detected by the activity monitor) are taken into account as well.

Preferably, a risk assessment unit 120 calculates the daily total amount of physical activity during active and rest period and compares the result to the previous day or to previous days. The system 100 may preferably monitor the physical activity pattern of the patient. The system 100 may preferably analyze the change in total amount of physical activity during both active and rest periods.

Figure 7:
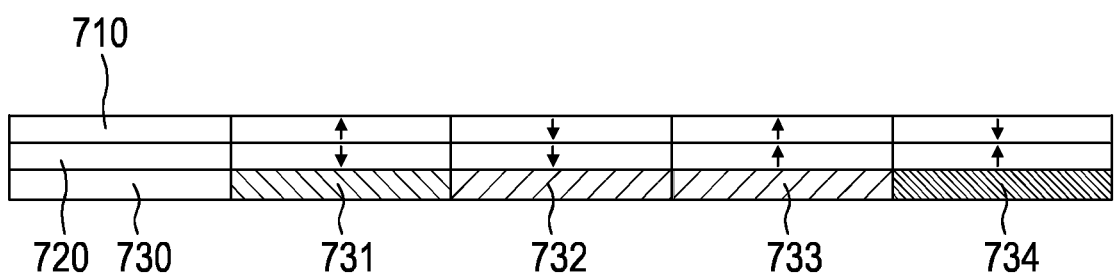
FIG. 7 shows schematically and exemplarily a traffic light warning system to provide warning indication based on the change in total amount of physical activity compare to day/days before.

A simple traffic light warning system 700 such as, e.g., the one shown in FIG. 7 may be used to provide a warning indication, or stability classification, to the patient or to the clinician in view of the symptoms of the patient. This information can then be used to classify whether the patient is at risk for an exacerbation and/or hospitalization. For instance, a patient whose physical activity during the active period 710 stays roughly the same or increases (denoted by an arrow pointing upward) while the patient's physical activity during the rest period decreases (denoted by an arrow pointing downward) over time may be classified stable (and e.g., labeled by a green color code 731). On the other hand, a patient whose physical activity during the active period decreases while the patient's physical activity during the rest period increases over time may be classified unstable (and e.g., labeled by a red color code 734). A patient falling into neither category (e.g., physical activity decreases during both active and rest periods, or physical activity increases during both active and rest periods) may be classified as undecided (and e.g., labeled by a yellow color code or by respective individual labels 732 and 733). For patients classified as unstable, there is an increased risk of hospital readmission so that a warning indication may be issued to the patient or to the clinician. Preferably, each day's classification is logged in a database and/or communicated to the patient's physician for review. Based on the classification result, the physician may decide to contact the patient for a check-up procedure. Preferably, based on the classification result, the physician may decide to arrange for a readmission of the patient.

The traffic light warning system may also be based on the absolute value of activity counts during active and rest periods, as indicated in the example shown in FIGS. 3 and 4. Namely, a patient's activity during active hours may be compared to a first activity level, and the patient's activity data during rest hours may be compared to a second activity level. (Typically, the first activity level is higher than the second activity level.) If the patient's activity during active hours is less than the first activity level and if the patient's activity during rest hours is more than the second activity level, the patient may be classified as unstable. If the patient's activity during active hours is equal to or more than the first activity level and if the patient's activity during rest hours is less than the second activity level, the patient may be classified as stable. A patient falling into neither category (e.g., physical activity above first activity level during active period and above second activity level during rest period, or physical activity below first activity level during active period and below second activity level during rest period) may be classified as undecided (and e.g., labeled by a yellow color code). As noted above, for patients classified as unstable, there is an increased risk of an exacerbation and/or hospital readmission so that a warning indication may be issued to the patient or to the clinician prior to the event occurring.

Preferably, the "first activity level" represents a threshold to which active period activity data (i.e., the first activity data) are compared. In one example, this threshold would be set to a mean active period activity count of a stable patient. That way, if the first activity data are higher than the "first activity level", the patient is more active than an average stable patient during active periods. Likewise, if the first activity data are lower than the "first activity level", the patient is less active than an average stable patient during active periods. The "second activity level" represents a threshold to which rest period activity data (i.e., the second activity data) are compared. In another example (which may be equal to or different from the example referred to above), this threshold would be set to a mean rest period activity count of a stable patient. That way, if the second activity data are higher than the "second activity level", the patient is more active than an average stable patient during rest periods. Likewise, if the second activity data are lower than the "second activity level", the patient is less active than an average stable patient during rest periods. Note that the term "activity level" does not necessarily imply that the "level" is an activity (measured in counts/min). For instance, having regard to the ratio approach described herein above, the "activity level" would correspond to a unit-less number.

The traffic light warning system may also be based on an absolute value of ratios of activity counts during active and rest periods, as indicated in the example shown in FIGS. 5 and 6. Namely, a ratio of a patient's activity during active over the patient's activity data during rest hours may be compared to a ratio activity level. The ratio activity level may be determined, e.g., from COPD patients falling into Group 1 or Group 2 mentioned above. If the ratio for a given patient is less than the ratio activity level, the patient may be classified as unstable. If the ratio for a given patient is equal to or more than the ratio activity level, the patient may be classified as stable, i.e., a lower risk of an exacerbation and/or readmission. As noted above, for patients classified as unstable, there is an increased risk of an exacerbation and/or hospital readmission so that a warning indication may be issued to the patient or to the clinician. In addition and/or alternatively to the ratio also the percentage sleep activity count to total day activity count could be used.

Figure 8:
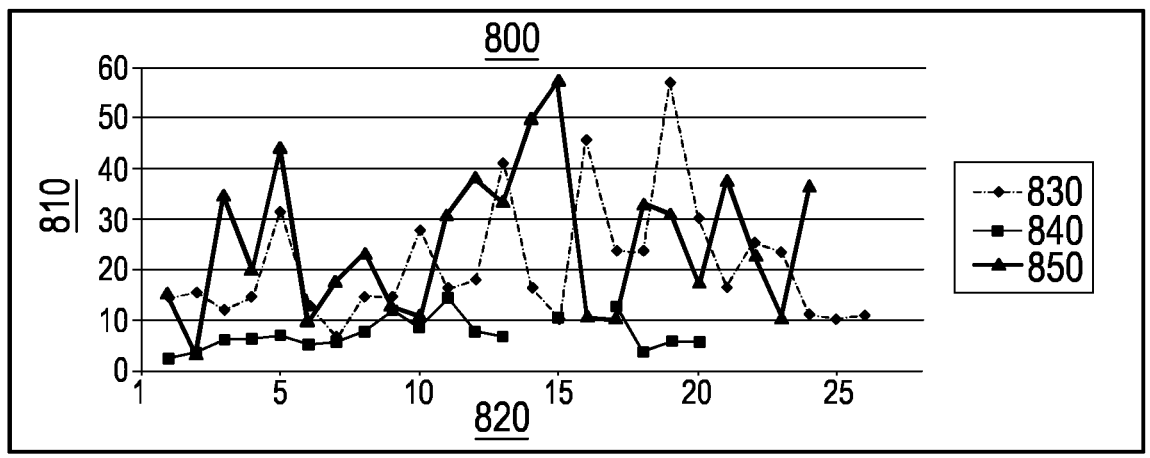
FIG. 8 shows schematically and exemplarily the ratio of mean awake activity count and mean sleep activity count for two stable patients and one unstable patients.

Graph 800 of FIG. 8 shows schematically and exemplarily the ratio of mean awake activity count and mean sleep activity count (on axis 810) for two stable patients 830, 850 and one unstable patient 840 with regard to the number of days post discharge (on axis 820). Patient 830 and patient 850 had no exacerbation or COPD readmission within one month-post discharge. Patient 820 had a COPD readmission 22 days post-discharge. Patient 820 has a lower ratio and less variation compared to patient 830 and patient 850.

Figure 9:
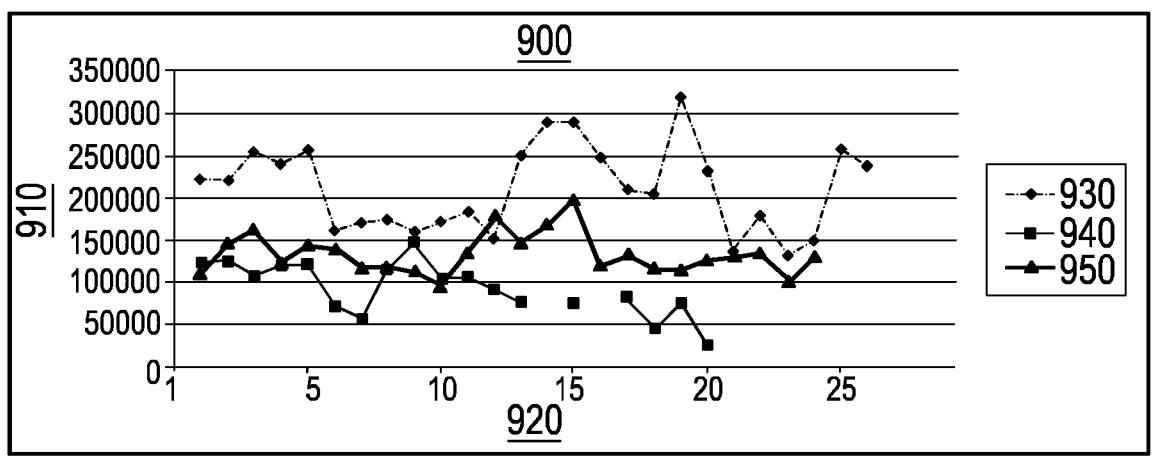
FIG. 9 shows schematically and exemplarily the difference between awake activity count and sleep activity count for two stable patients and one unstable patient.

Graph 900 of FIG. 9 shows schematically and exemplarily the difference between of awake activity count and sleep activity count (on axis 910) for two stable patients 930, 950 and one unstable patient 940 with regard to the number of days post discharge (on axis 920). Patient 930 and patient 950 had no exacerbation or COPD readmission within one month-post discharge. Patient 940 had a COPD readmission 22 days post-discharge. Nearer the time of the readmission, patient 940 has a lower difference between awake and sleep activity, indicating that the daily awake activity is lower than for a stable situation, and that the daily sleep activity is higher than for a stable situation. The awake activity for an unstable patient may also stay roughly the same (rather than decrease), whilst the night activity increases. In such a situation, the relative activity (i.e., ratio or difference) between day and night still includes information on the patient's risk of an exacerbation and/or hospitalization.

An example application of the invention is in activity monitoring applications and activity monitoring devices. It is specifically designed for use in COPD, but it can also be used for other chronic diseases where staying active is important.

The physical activity measurement unit may comprise one or more accelerometers. The system may comprise one or more processors to compute ratios and/or differences of activity data, and/or to compare the computed result to an activity level.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Determinations like measuring the patient's physical activity during at least part of an active period of time to gather first activity data, measuring the patient's physical activity during at least part of a rest period of time to gather second activity data; and/or detecting the onset of the exacerbation and or a hospital readmission risk based on predetermined criteria, et cetera performed by one or several units or devices can be performed by any other number of units or devices. For example, detecting the onset of the exacerbation and/or a hospital readmission risk based on predetermined criteria can be performed by a single unit of by any other number of different units. The determinations and/or the control of the system for predicting an onset of an exacerbation in a COPD patient and/or a hospital readmission risk in accordance with the above described method for detecting hospitalization risk can be implemented as program code means of a computer program and/or as dedicated hardware.

In addition, multiple parameters may be used to predict an onset of exacerbation and/or a re-admission. That is, detection of an onset of the exacerbation and/or risk of hospital re-admission may be based not only on one criterion but on a number of predetermined criteria comprising inter alia a difference calculation of a patient's physical activity during at least part of an active period and part of a rest period.

A computer program may be stored/distributed on a suitable medium, such as an optical storage medium or a solid-state medium, supplied together with or as part of other hardware, but may also be distributed in other forms, such as via the Internet or other wired or wireless telecommunication systems. The term "computer program" may also refer to embedded software.

Any reference signs in the claims should not be construed as limiting the scope.

The present invention relates to an apparatus, a system, method, and computer program for assessing the risk of an exacerbation and/or hospitalization. A patient's physical activity is measured (e.g., by an accelerometer) during an active period of time (e.g., during awake hours) and during a rest period of time (e.g., during sleep hours) to gather first and second activity data. A risk of exacerbation and/or hospitalization is assessed (e.g., by a risk assessment unit) based on an expression involving the respective activity data during active and rest periods fulfilling a predetermined relationship with respect to a predetermined activity level. For instance, low activity data during active periods and high activity data during rest periods indicates an increased risk of exacerbation and/or hospital readmission for the patient.

The invention claimed is:

1. An apparatus for assessing the risk of an exacerbation and/or hospitalization of a subject, said apparatus comprising:
    a first accelerometer having a first sensitivity;
    a second accelerometer having a second sensitivity, different from the first sensitivity;
    an input unit for receiving first and second activity data for said subject from the first and second accelerometers, respectively, wherein said first activity data is indicative of said subject's physical activity during at least part of an active period of time, wherein said second activity data is indicative of said subject's physical activity during at least part of a rest period of time; and
    a risk assessment unit configured to detect an onset of the exacerbation based on predetermined criteria, wherein the predetermined criteria comprises the condition that an expression involving the first activity data and/or the second activity data fulfills a predetermined relationship with respect to a predetermined activity level,
        the apparatus being configured to determine a ratio between first activity data and second activity data, wherein the apparatus is configured to compare the ratio to a ratio activity level, wherein the predetermined criteria comprise the condition that the ratio is lower than the ratio activity level.

2. The apparatus of claim 1, wherein the first activity data corresponds to average activity data of said subject during at least part of the active period;
    and/or wherein the second activity data corresponds to average activity of said subject during at least part of the rest period.

3. The apparatus of claim 1, wherein the first activity data corresponds to average activity data of said subject during the entire active period; and/or
wherein the second activity data corresponds to average activity of said subject during the entire rest period.

4. The apparatus of claim 1, wherein the apparatus is configured to compare the first activity data to past first activity data, wherein the past first activity data correspond to first activity data gathered on one or more previous days; and/or
wherein the apparatus is configured to compare the second activity data to past second activity data, wherein the past second activity data correspond to second activity data gathered on the one or more previous days.

5. The apparatus of claim 4, wherein the predetermined criteria comprise the conditions that:
    (1) the first activity data is lower than one or more of the past first activities, and
    (2) the second activity is higher than one or more of the past second activities.

6. The apparatus of claim 1, wherein the apparatus is configured to compare the ratio to past ratios, wherein the past ratios correspond to ratios between first activity data and second activity data gathered on one or more previous days.

7. The apparatus of claim 6, wherein the predetermined criteria comprise the condition that the ratio is smaller than one or more of the past ratios.

8. A system for assessing the risk of an exacerbation and/or hospitalization of a subject, the system comprising:
    a physical activity measurement unit;
    wherein the physical activity measurement unit is configured to measure said subject's physical activity during at least part of an active period of time to gather first activity data;
    wherein the physical activity measurement unit is further configured to measure the subject's physical activity during at least part of a rest period of time to gather second activity data; and an apparatus as defined in claim 1; wherein said input unit of said apparatus is configured to receive said first and second activity data from said physical activity measurement unit.

9. An apparatus as in claim 1, wherein the ratio activity level comprises an average activity level of a patient group.

10. An apparatus as in claim 1, wherein the apparatus is further configured to determine a stability classification for the subject based on the comparison of the ratio to the ratio activity level, and further comprising a display configured to display the determined stability classification.

* * * * *